(12) United States Patent
Gassmann

(10) Patent No.: US 7,871,507 B2
(45) Date of Patent: Jan. 18, 2011

(54) MEDIUM FOR ENHANCED STAINING OF SINGLE STRAND NUCLEIC ACIDS IN ELECTROPHORESIS

(75) Inventor: Marcus Gassmann, Karlsruhe (DE)

(73) Assignee: Agilent Technologies, Inc., Santa Clara, CA (US)

(*) Notice: Subject to any disclaimer, the term of this patent is extended or adjusted under 35 U.S.C. 154(b) by 379 days.

(21) Appl. No.: 11/796,779

(22) Filed: Apr. 30, 2007

(65) Prior Publication Data
US 2008/0251380 A1 Oct. 16, 2008

(30) Foreign Application Priority Data
Apr. 10, 2007 (EP) .................. 07105851

(51) Int. Cl.
*G01N 27/453* (2006.01)
*G01N 27/26* (2006.01)
(52) U.S. Cl. .................. 204/468; 204/606; 204/461; 204/616
(58) Field of Classification Search .................. 204/450, 204/456, 469, 606, 616, 461, 468; 205/775
See application file for complete search history.

(56) References Cited

U.S. PATENT DOCUMENTS 4,950,708 A * 8/1990 Hochstrasser .................. 524/728
6,938,476 B2 * 9/2005 Chesk .................. 73/290 R
2004/0204523 A1 * 10/2004 Kratzmeier .................. 524/211
2006/0057566 A1 * 3/2006 Van Ness et al. .................. 435/6

OTHER PUBLICATIONS

Althaus et al. ("Two-dimensional gel electrophoresis of myelin and oligodendroglial proteins solubilized by a mixture of tetramethylurea and dimethylethyleneurea", Electrophoresis 1983, 4, 347-353).*
Barker et al. ("Ureas as Solvents for Chemical Investigations", Angew. Chem. Inr. Ed. Engl. 18, 503-507, 1979).*
Khurgin et al. ("Investigation of Intermolecular Interactions in Solutions By Means of Millimeter-Wave Spectroscopy",1990 Plenum Publishing Corporation, pp. 265-270).*
Product Information of Dimeric Cyanine Nucleic Acid Stains, Jan. 2000 ("Product Information").*

* cited by examiner

*Primary Examiner*—Alexa D Neckel
*Assistant Examiner*—Jennifer Dieterle

(57) ABSTRACT

A medium is provided, being adapted to be applied in electrophoretic separation of nucleic acids. The medium comprises a staining reagent adapted to stain nucleic acids. Said medium further comprises a urea derivative, adapted to interact with said staining reagent and thereby providing an enhanced staining of said nucleic acids. Further, an electrophoresis device is provided, adapted to perform electrophoretic separation of nucleic acids, comprising the before medium and comprising electrodes for applying an electrical field across the medium. A method to perform electrophoresis using the before electrophoresis device and medium is provided.

27 Claims, 6 Drawing Sheets

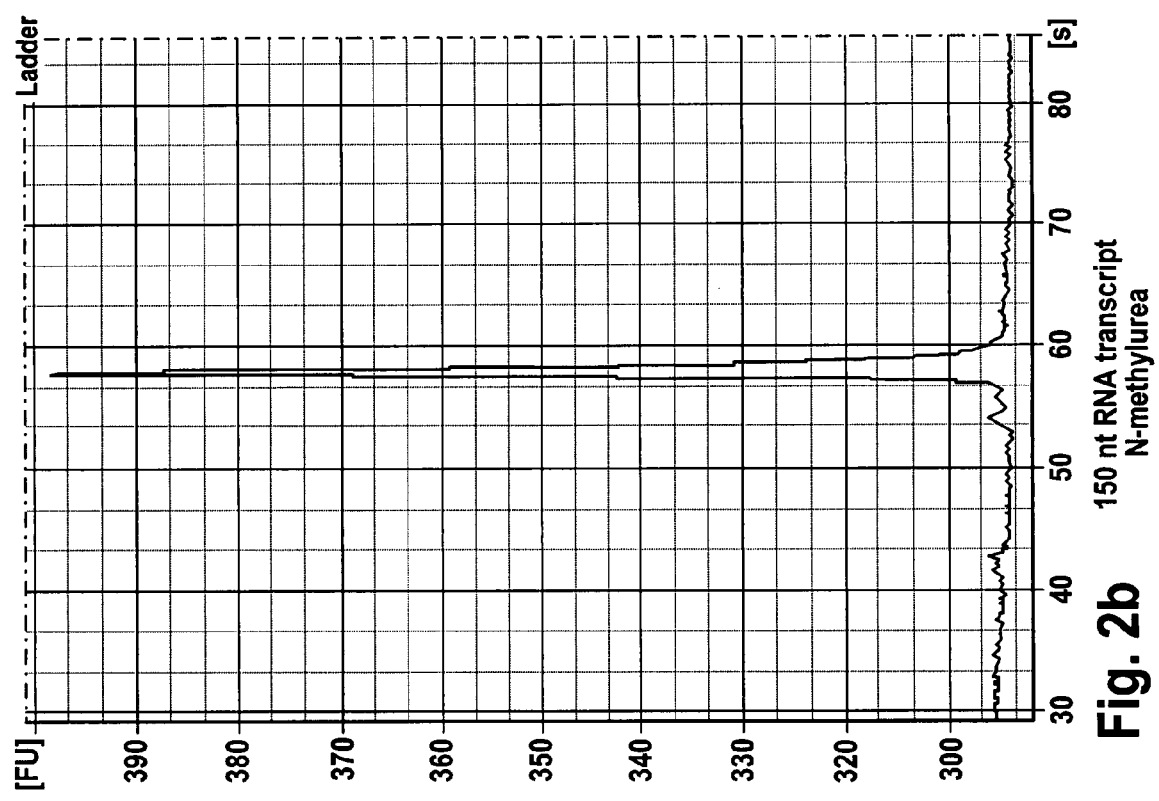
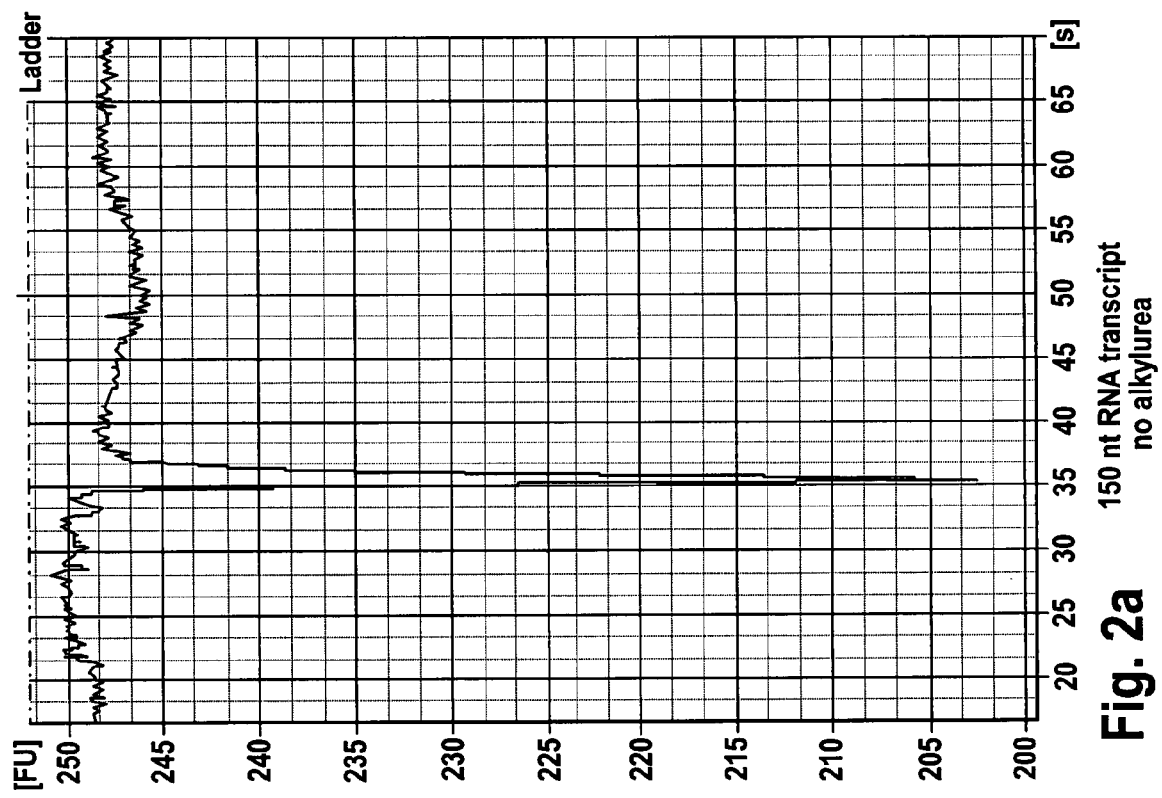

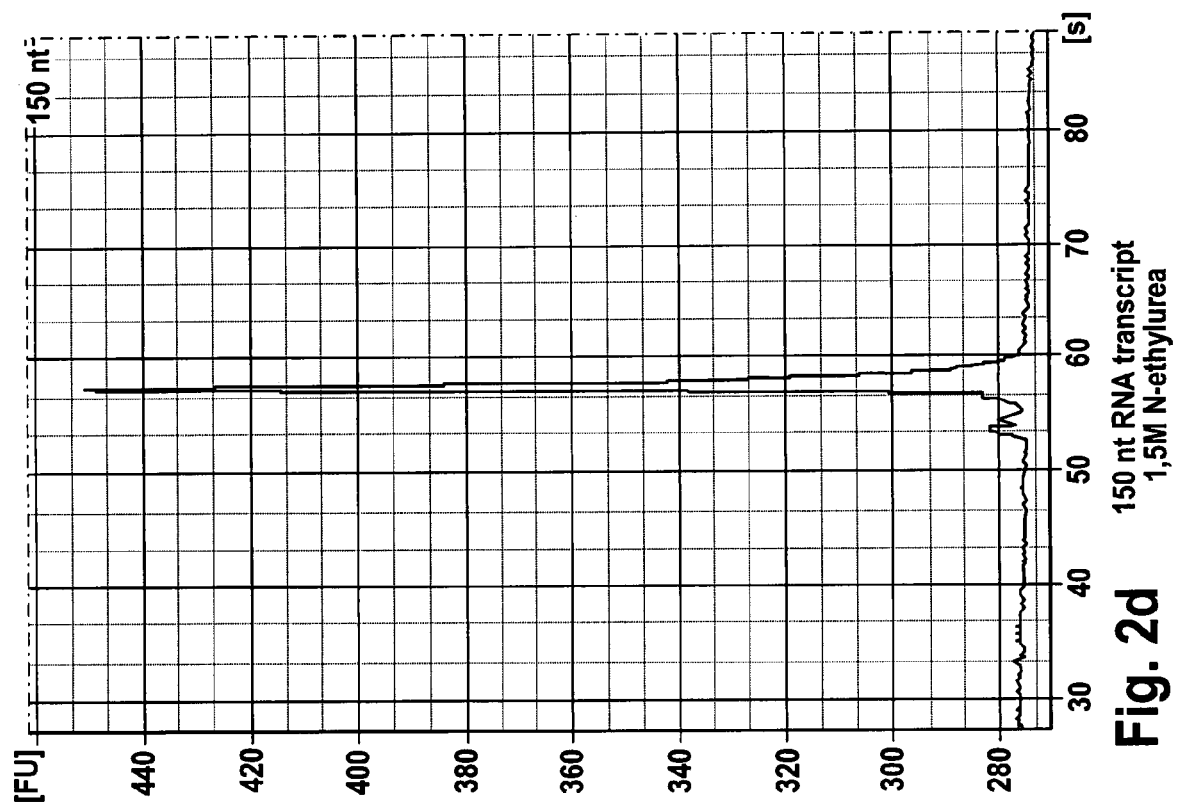
Fig. 2c  150 nt RNA transcript N,N-dimenthylurea
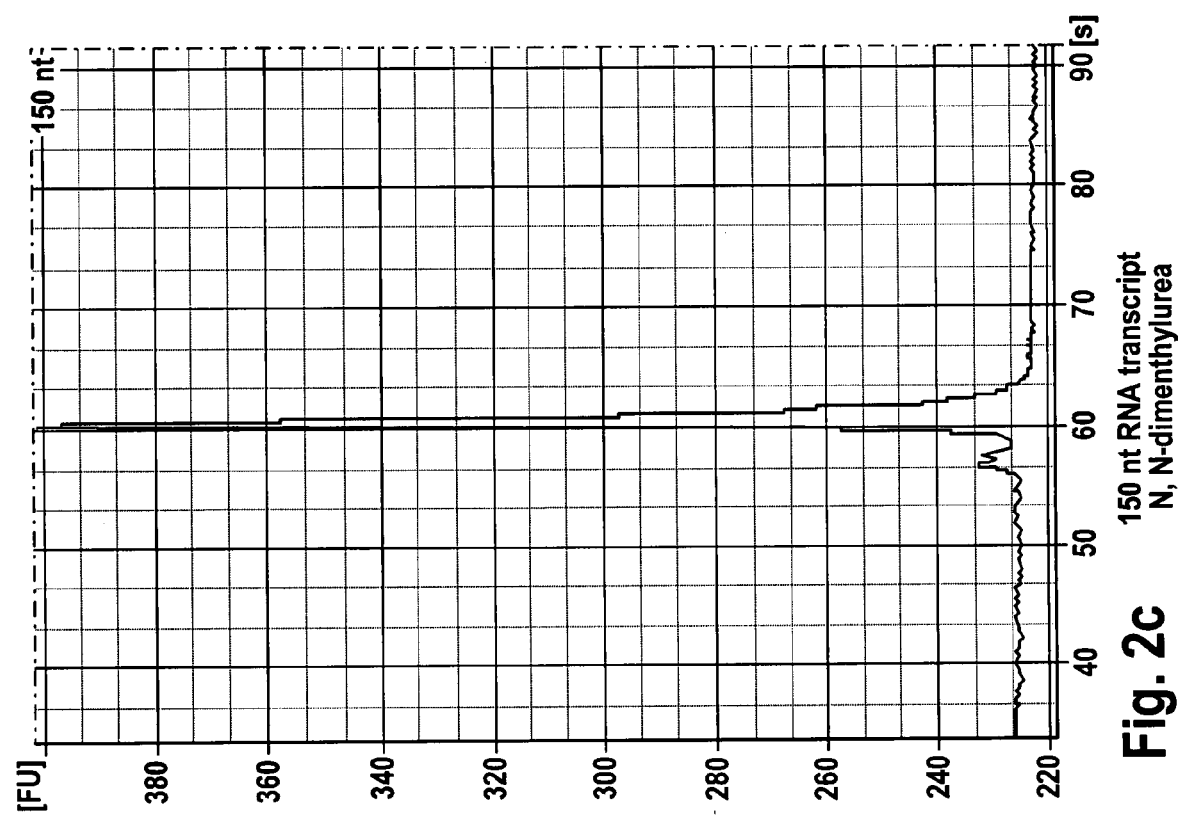
Fig. 2d  150 nt RNA transcript 1,5M N-ethylurea

MEDIUM FOR ENHANCED STAINING OF SINGLE STRAND NUCLEIC ACIDS IN ELECTROPHORESIS

FIELD OF THE INVENTION

The present invention relates to electrophoresis.

BACKGROUND ART

Electrophoresis is a widely known technique for separation of biomolecules such as nucleic acid or proteins. Generally, electrophoresis is understood as being migration of charged molecules through a sieving material while an electrical field is applied to said material. According to their different electrophoretic mobility, and, hence, their velocity within said sieving material, a mixture of differently sized and electrically charged molecules becomes separated into fractions of molecules having the same mobility. Said electrophoretic mobility is a physical-chemical function of the molecule in the respective medium, it depends on a plurality of chemical, electrochemical and physical factors such as the aforementioned size and charge of molecules, and further on the characteristics of the carrier material such as pore width. The sieving material may be a gel or a liquid.

Selection of a suitable sieving matrix permits an optimized separation of biomolecules having different biochemical properties: Agarose is a preferred sieving material to perform separation of DNA, whereas protein separation is often carried out in, e.g., polyacrylamide. Analysis of an unknown sample further comprises calibration using a standard detection, particularly optical detection. Said last detection technique is favored due to its reliability, rapidity and direct-to-apply option. Optical detection of biomolecules requires visualization of the separated fractions, which is conveniently done using a staining substance for the molecules to be visualized. Due to physical and chemical properties of said staining substances which are generally suitable for staining specific biochemical molecules, said staining substances are not sufficiently reliable in staining the whole range of components comprised in one single sample similarly. Typical staining substances for nucleic acids like DNA and RNA are intercalating dyes. A plurality of works has been dedicated to perform highly sophisticated electrophoresis.

U.S. Pat. No. 6,835,773 B2 to M. Kratzmeier, e.g., is focusing on electrophoretical analysis of proteins: A minute sample of proteins is introduced in an electrophoresis medium which comprises N-methylurea and a polyacrylamide gel, which is adapted do be subjected to an electrical field being applied across the medium.

DISCLOSURE

It is an object of the invention to provide an improved electrophoretic analysis of nucleic acids. The object is solved by the independent claims. Further embodiments are shown by the dependent claims.

Embodiments of the present invention provide devices and methods for use in electrophoresis, enabling reliable staining of the whole range of molecule sizes which still withstand highly resolved electrophoresis.

According to embodiments of the present invention, a medium is provided which may be used in electrophoretic separation and analysis of nucleic acids and which is composed of a staining compound and at least one urea derivative, capable of modulating the staining compound such that advantageously even nucleic acids having a short length become stained, thereby resulting advantageously in an improved resolution and, thus, analysis in electrophoresis. In particular, single stranded nucleic acids such as single stranded RNA or DNA oligonucleotides become stained when using said medium containing a urea-activated staining agent.

The medium mentioned before is preferably used in an electrophoresis gel, which is pointed out in another embodiment of the present invention. Said gel is adapted to suspend the staining agent and the urea derivative, thereby permitting in situ modulation of the staining agent by the urea derivative during separation. The staining agent may preferably be an intercalating fluorescent dye.

Another embodiment of the present invention depicts the variety of possible staining enhancers; advantageously a plurality of urea derivatives may be employed.

According to additional embodiments of the invention, the medium being suitable for improving staining of nucleic acids such as single stranded RNA and DNA of even small and very small sizes is comprised in an electrophoresis device, which is adapted to perform electrophoretic separation of said biochemical molecules. The electrophoresis device further provides an equipment to apply a desired electrical field across said medium, such that an effective and reliable electrophoresis is performed.

Further, embodiments of the present invention refer to methods of performing electrophoresis using the advantageously improved electrophoresis medium.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings.

FIG. 2a shows an electropherogram of an RNA transcript sample with the molecular size of 150 nucleotides in the absence of any urea derivative, FIG. 2b shows an electropherogram of the sample of FIG. 2a in the presence of N-methylurea, FIG. 2c shows an electropherogram of the sample of FIG. 2a in the presence of N,N'-dimethylurea, FIG. 2d shows an electropherogram of the sample of FIG. 2a in the presence of N-ethylurea.

Figure 1B:
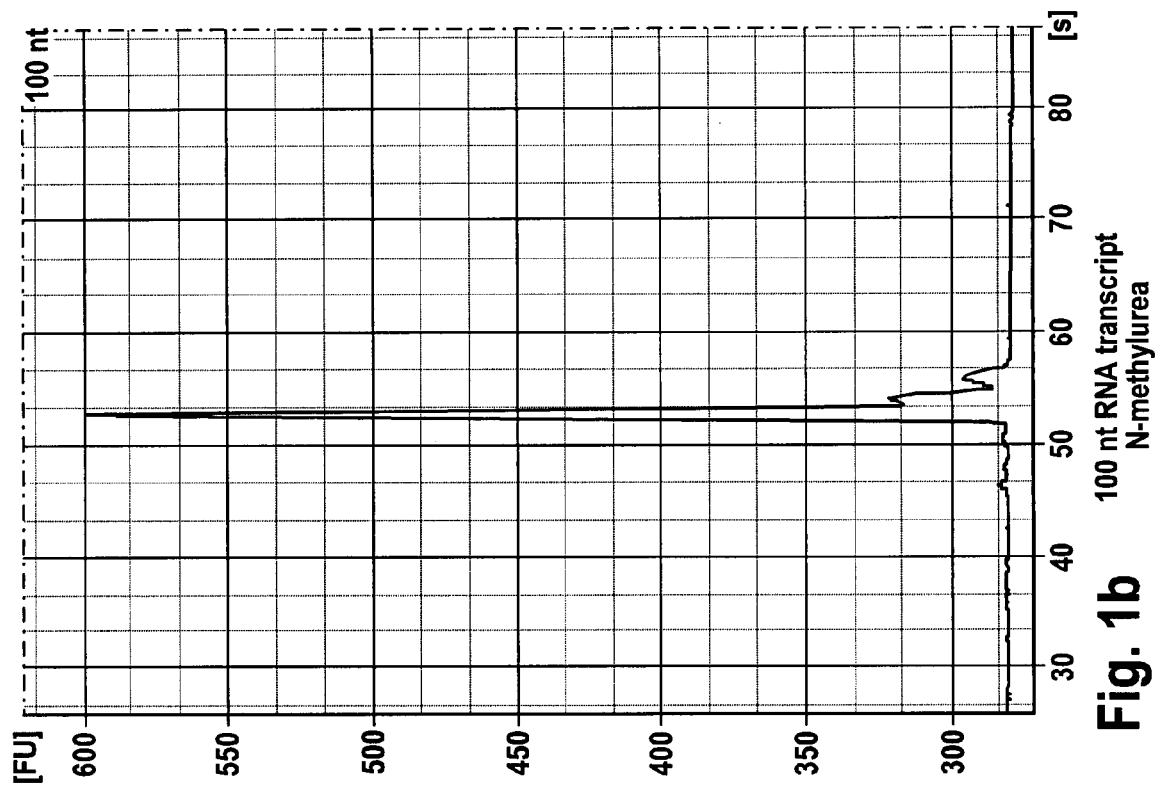
FIG. 1b shows an electropherogram of the sample of FIG. 1a in the presence of N-methylurea.

The embodiments shown in the following refer to an improved staining of nucleic acids in electrophoresis. A medium is provided, which is specifically designed for electrophoretic separation of nucleic acids. It comprises a staining reagent in order to stain the nucleic acids and, furthermore, a urea derivative, which is capable of interacting and modulating, respectively, the staining reagent such that an increased staining activity is obtained, and thereby an enhanced staining of said nucleic acids is achieved. In order to perform mobility based separation, an electrophoresis gel suitable for nucleic acid separation is comprised, too, which is adapted to suspend the staining agent and the urea derivative.

The afore described medium is in particular useful in separation and detection of single stranded nucleic acids, which under conventional conditions withstand staining in some extend, such that reliable visualization is impossible or at least hindered and difficult. The medium of the embodiments of the present invention enables staining of single stranded RNA, in particular of single stranded RNA being composed of 5 to 200 nucleotides or less, it is even possible to stain single stranded RNA being composed of 5 to 150 nucleotides and even less, such as, single stranded RNA being composed of only 5 to 100 nucleotides or 5 to 50 nucleotides.

A urea derivative comprises urea itself and compounds derived from urea. A urea derivative as it is to be understood according in the herein given description and the claims has the general formula $R_1R_2N—CO—NR_3R_4$. $R_1$. Herein, $R_1$, $R_2$, $R_3$ and $R_4$ are residues which are attached to nitrogen. These residues may be single hydrogen atoms or they may be alkyls. An alkyl in the herein referred derivative may comprise up to 20 carbon molecules. Of course, the residues $R_1$, $R_2$, $R_3$ and $R_4$ may be composed identically or differently. Preferred urea derivatives are N-methylurea, N,N'-dimethylurea and N-ethylurea. Further, the skilled person is used to prepare suitable mixtures of the aforesaid urea derivatives which may comprise two or more different urea derivatives.

The medium according to embodiments of the present invention comprises urea and urea derivatives, respectively, in concentrations ranging from 0.01 to 8.0 moles per liter. Preferred concentrations range from 0.05 to 3.5 moles per liter and most preferred concentrations range from 0.5 to 3.0 moles per liter. Further it comprises an electrophoresis gel such as Agarose, which is an excellent electrophoresis gel for nucleic acid electrophoresis. In some embodiments, the gel can be selected from polyacrylamide, polydimethylacrylamide, polyvinylpyrrolidine, and polyethyleneoxide.

The herein described medium for use in electrophoresis is in particular an excellent device to be used in small RNA assays, which assays are designed to perform analysis of RNA, particularly of single stranded RNA, having lengths ranging from of 5 to 200 nucleotides. Examples below depict the use of the medium of embodiments of the present invention in applications for analysis of 150 nucleotides RNA and 100 nucleotides respectively. Even RNA consisting of a number below 100 RNA, such as, e.g. 50 nucleotides may be subjected to analysis using the aforesaid medium resulting in reliable analysis results.

A most promising mixture of two intercalating fluorescent dyes in small RNA assays comprises two commercially available fluorescent dyes SYTO 61 (Invitrogen Corporation) and TOTO-3 (Invitrogen Corporation). An embodiment of a medium of the present invention is obtained by adding one of N-methylurea, N,N'-dimethylurea and N-ethylurea to the mixture, said urea derivative being present in a concentration of about 1 mole per liter. A small RNA assay equipped with the afore described medium is suitable for performing analysis of single stranded RNA species but also for separation and analysis of single stranded DNA oligonucleotides. Linear polydimethylacrylamide for example is perfectly suitable to solve the fluorescent dyes SYTO 61 and TOTO-3, and further urea derivatives and, hence, provides an optimal base to allow interaction of said urea derivatives with said staining substances. Accordingly, urea and urea derivatives, respectively, may lead to an in-situ activation of the staining substances during electrophoretic separation. This can lead to an enhanced resolution of an electropherogram obtained using the medium of an embodiment of the present invention and, additionally, to an improved, reduced baseline noise.

The medium of the herein described embodiments of the present invention is used in electrophoresis devices such as micro devices or assays, respectively.

Methods to perform electrophoresis with an electrophoresis device according to an embodiment of the present invention are carried out as the ones performed with conventional electrophoresis devices. Generally, the electrophoresis devices will have to be equipped with the medium of the embodiment of the present invention before electrophoresis is done; conventionally the electrophoresis device manufacturer or the assay manufacturer may provide the appropriate devices, using the herein described media.

EXAMPLE 1

Figure 1A:
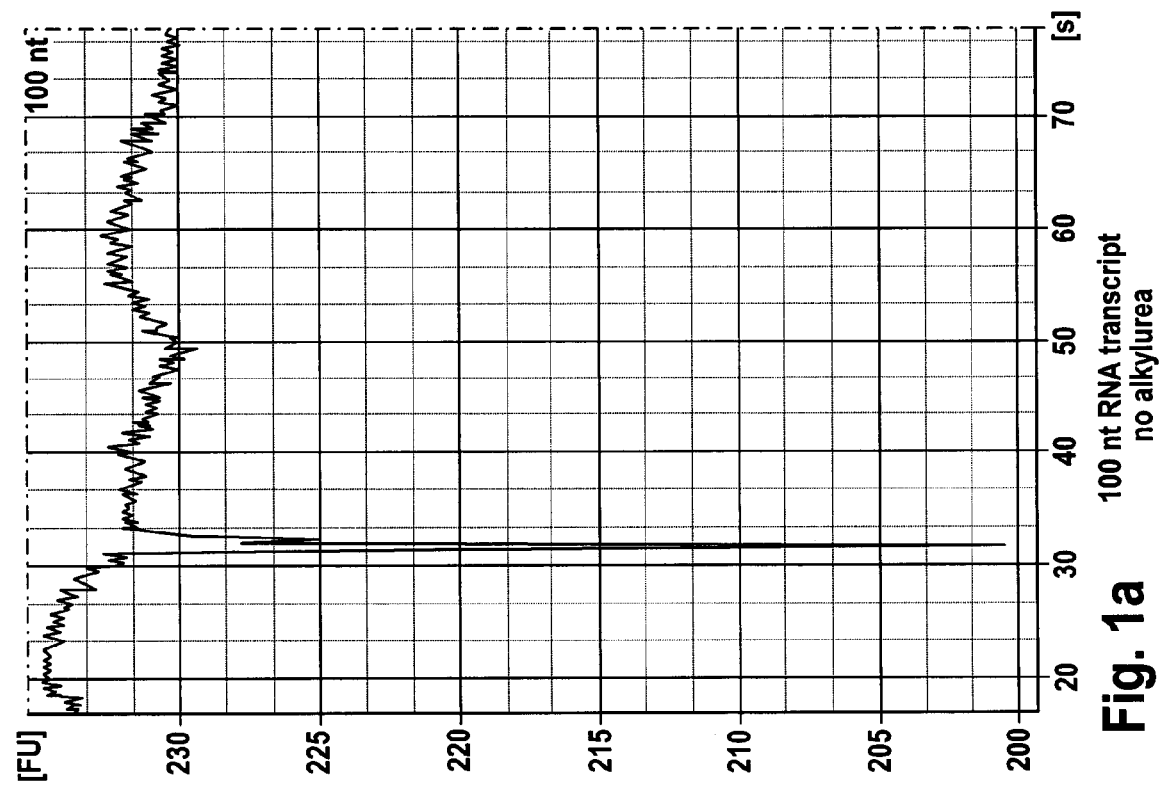
FIG. 1a shows an electropherogram of an RNA transcript sample with the molecular size of 100 nucleotides, the electropherogram being taken in the absence of any urea derivative.
Figure 1D:
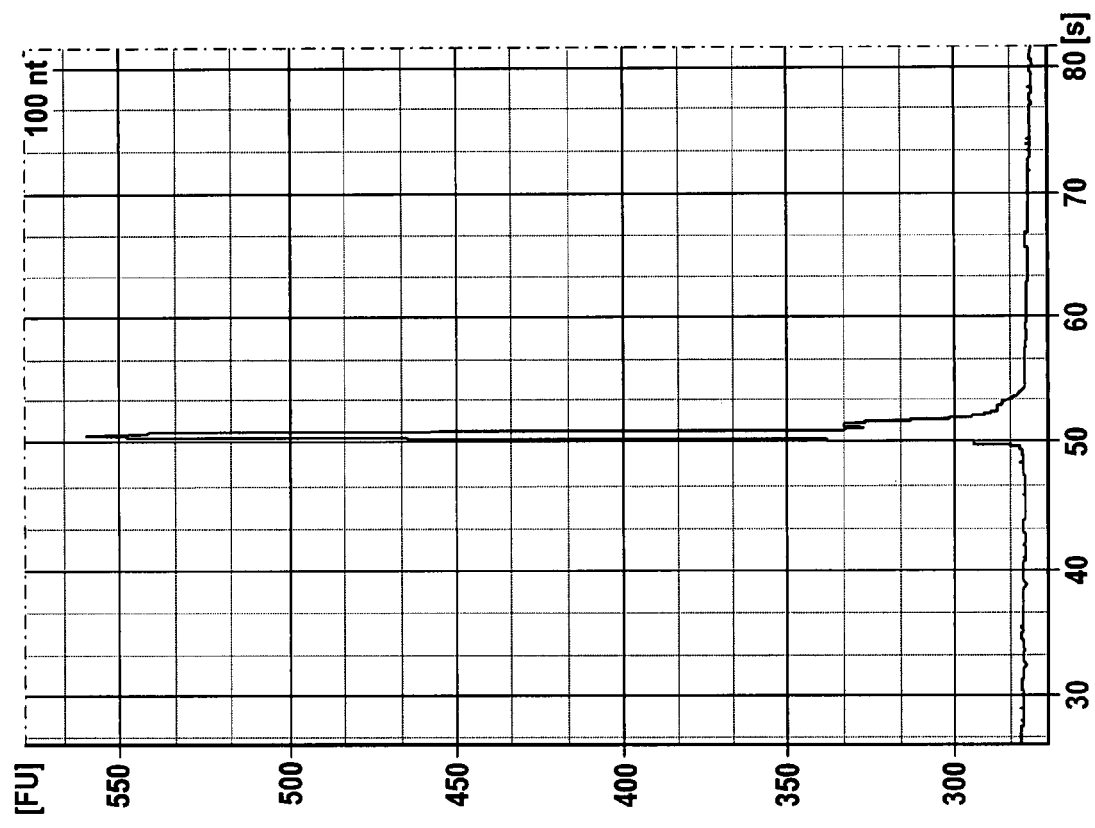
FIG. 1d shows an electropherogram of the sample of FIG. 1a in the presence of N-ethylurea.
Figure 1C:
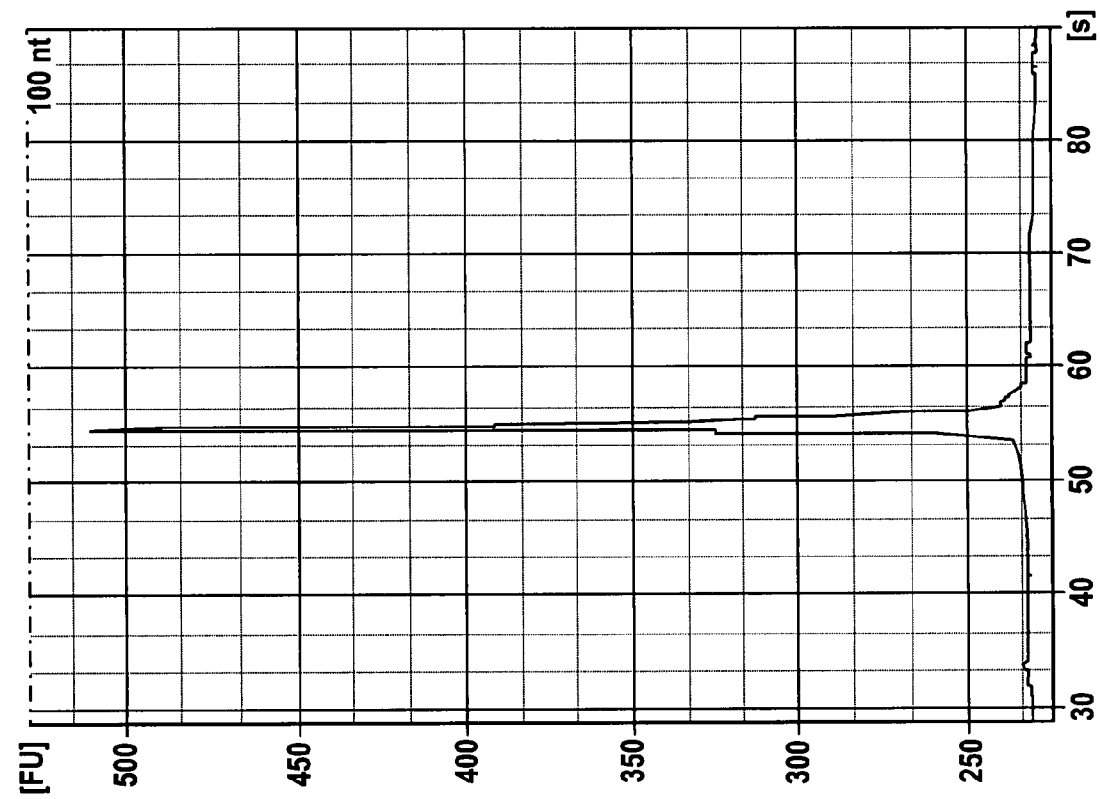
FIG. 1c shows an electropherogram of the sample of FIG. 1a in the presence of N,N'-dimethylurea.

In FIGS. 1a to 1d, electropherograms of an RNA transcript sample with the molecular size of 100 nucleotides are shown. FIG. 1a depicts, that electrophoretic separation of said RNA transcript being taken in the absence of any urea derivative leads to an enormous negative peak. A volume of the same sample has been subjected to microchip electrophoresis using a sieving gel comprising a solution of polydimethylacrylamide and N-methylurea. The result is shown in FIG. 1b: Obviously, the presence of N-methylurea led to conversion of said formerly negative peak and an electropherogram with a much better signal to noise ratio and a positive peak, indicating the 100 nt RNA transcript, is outlined. FIGS. 1c and 1d show the respective electropherograms achieved using N,N'-dimethylurea and N-ethylurea, indicating clearly, that usage of a urea derivative reduces the baseline noise and results in a positive peak showing perfect resolution.

EXAMPLE 2

FIG. 2a shows an electropherogram of an RNA sample with the molecular size of 150 nucleotides in the absence of any urea derivative. In FIGS. 2a to 2d, electropherograms of respective RNA transcript samples having 150 nucleotides are shown. FIG. 2a points out, too, that the absence of any urea derivative in electrophoretic separation of said RNA transcript leads to an enormous negative peak. FIG. 2b shows a volume of the same sample being subjected to electrophoresis using an electrophoresis gel comprising N-methylurea. The result shows clearly that the presence of N-methylurea results in a positive peak and to an electropherogram with a smoothed baseline. FIGS. 2c and 2d repeat the result obtained in the electropherogram of FIG. 1b: A volume of said sample of the above 150 nucleotides comprising RNA has been subjected to electrophoresis, too. The electropherograms achieved using N,N'-dimethylurea and N-ethylurea underline, that usage of a urea derivative reduces advantageously the baseline noise and results in a positive peak showing perfect resolution.

EXAMPLE 3

Figure 3B:
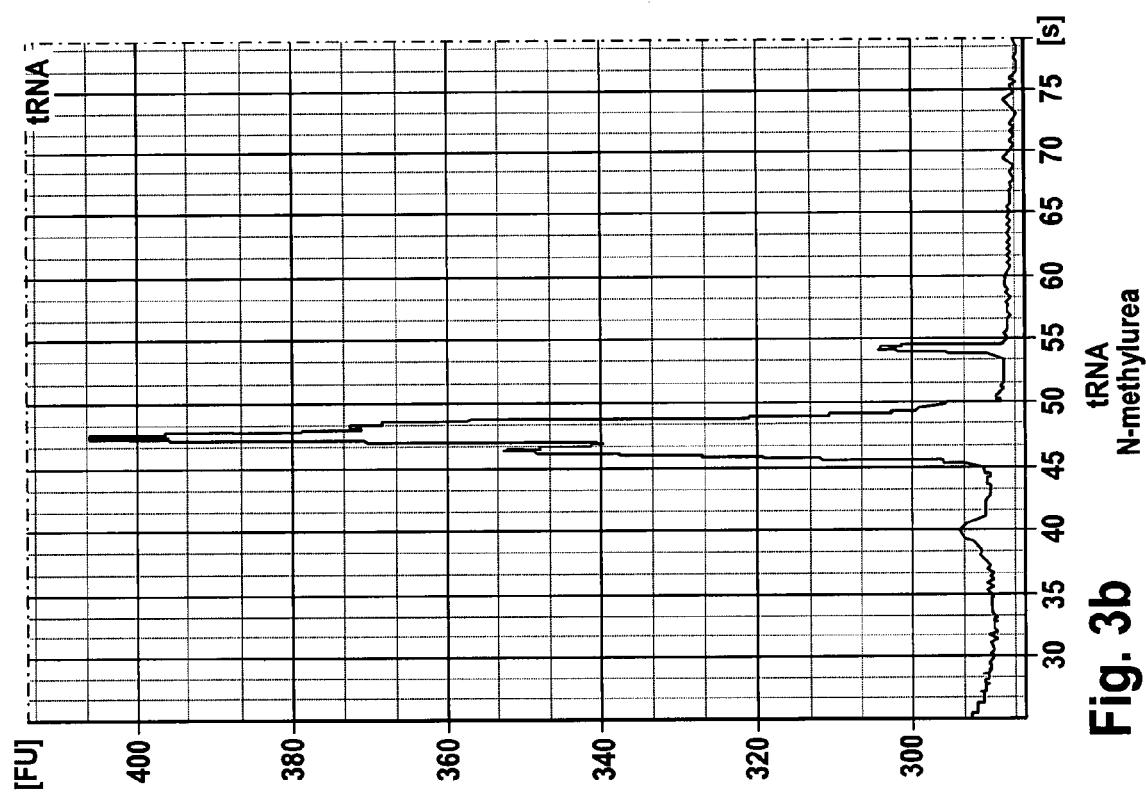
FIG. 3b shows an electropherogram of the sample of FIG. 3a in the presence of N-methylurea.
Figure 3A:
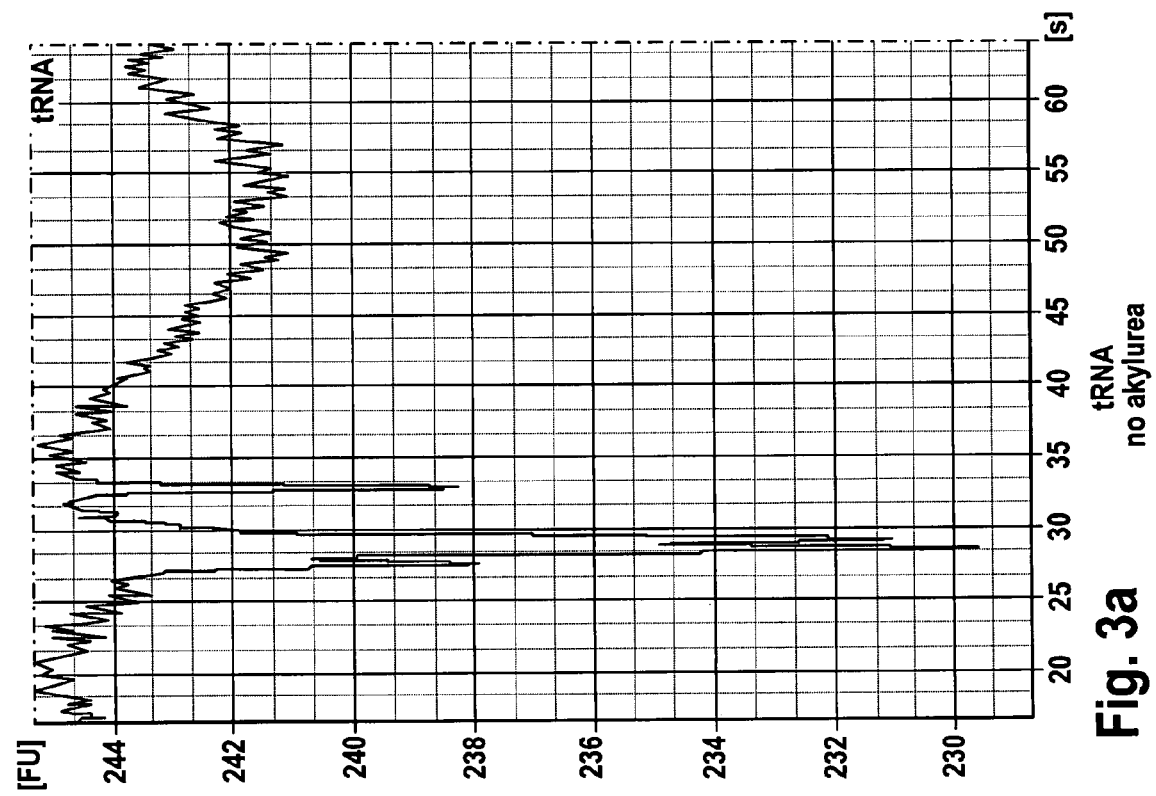
FIG. 3a shows an electropherogram of a transfer-RNA (tRNA) sample having in the absence of any urea derivative.
Figure 3D:
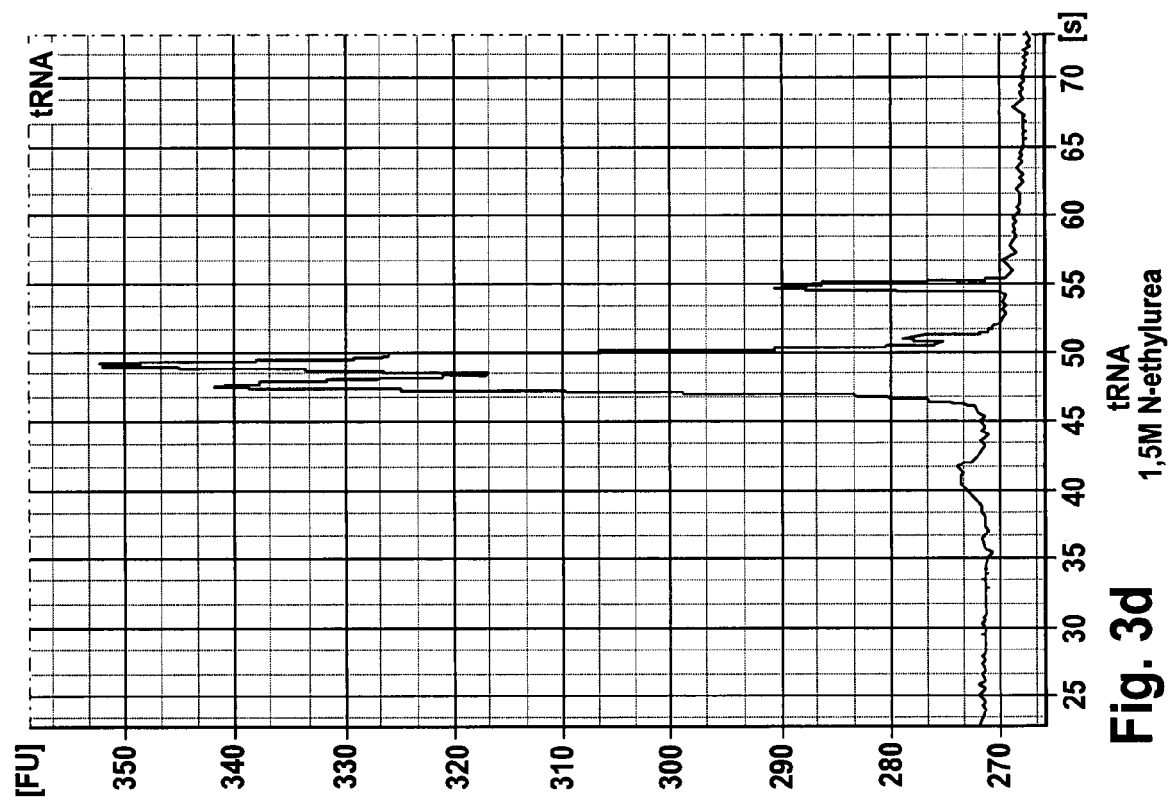
FIG. 3d shows an electropherogram of the sample of FIG. 3a in the presence of N-ethylurea.
Figure 3C:
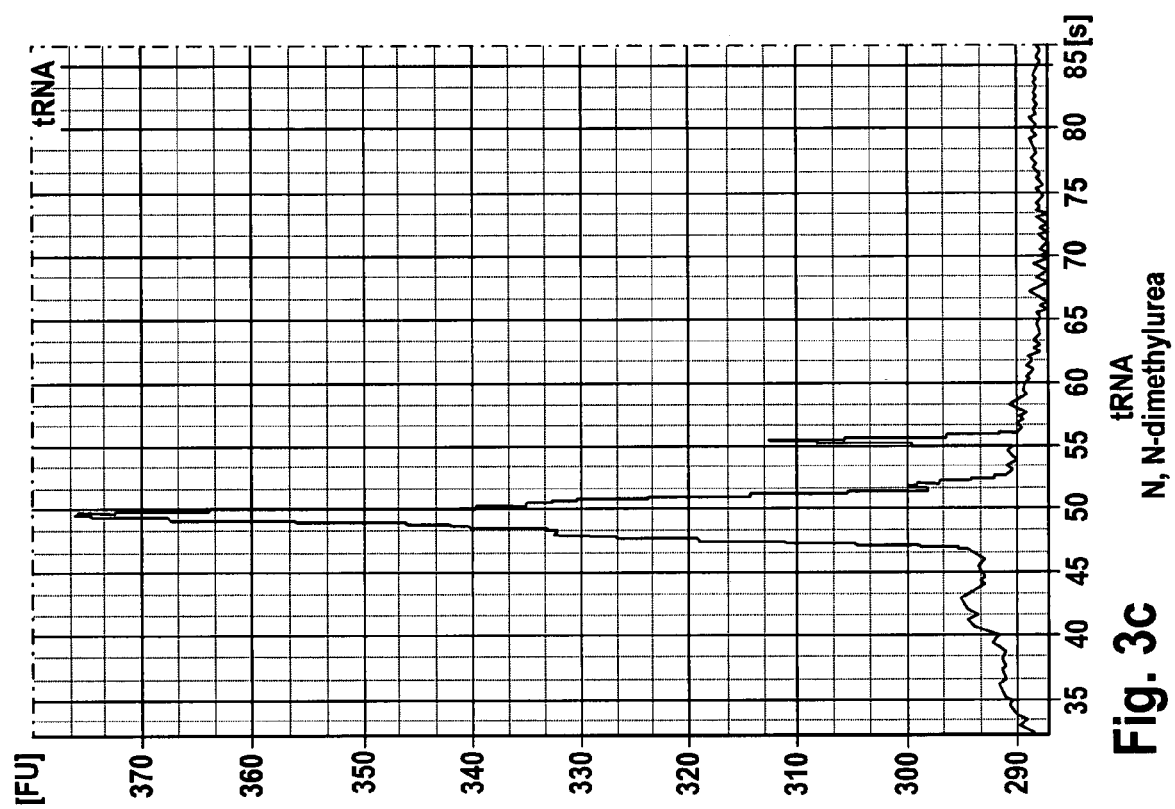
FIG. 3c shows an electropherogram of the sample of FIG. 3a in the presence of N,N'-dimethylurea.

In FIGS. 3a to 3d, electropherograms of a transfer-RNA (tRNA) sample were shown. FIG. 3a shows that performance of electrophoretic separation in absence of urea derivatives results in a heavily waved baseline, the tRNA peak is a negative peak. Due to a plurality of side peaks the main peak is indistinct. FIG. 3b, showing an electropherogram taken in the presence of N-methylurea, depicts a perfectly sharp positive tRNA-peak and a dramatically smoothed baseline. Similar results have been obtained using N,N'-dimethylurea and N-ethylurea, which can be seen in FIGS. 3c and 3d, respectively.

The invention claimed is:

1. A method of performing electrophoresis comprising:
   introducing a sample comprising nucleic acids into an electrophoresis device comprising an electrophoresis separation medium having at least one staining reagent for staining nucleic acids and at least one urea derivative for interacting with the staining reagent;
   wherein the electrophoresis device comprises electrodes for applying an electrical field across the separation medium; and
   operating the electrodes, thereby providing an electric field across the medium which is sufficient to separate the nucleic acids in the sample.

2. The method of claim 1, wherein the separation medium comprises a gel adapted to suspend the staining reagent and the urea derivative.

3. The method of claim 1, wherein the staining reagent is an intercalating dye.

4. The method of claim 1, wherein a mixture of at least two different urea derivatives is present.

5. The method of claim 1, wherein the urea derivative is N-methylurea, N,N'-dimethylurea, N-ethylurea, or a mixture thereof.

6. The method of claim 1, wherein the urea derivative is present in a concentration ranging from 0.01 to 8.0 mole per liter.

7. The method of claim 1, wherein the urea derivative is present in a concentration ranging from 0.05 to 3.5 mole per liter.

8. The method of claim 1, wherein the urea derivative is present in a concentration ranging from 0.1 to 3.0 mole per liter.

9. The method of claim 1, wherein the gel comprises polyacrylamide, polydimethylacrylamide, polyvinylpyrrolidine, or polyethyleneoxide.

10. The method of claim 1, wherein the urea derivative has a general formula $R_1R_2N\text{—}CO\text{—}NR_3R_4$, wherein each of $R_1$, $R_2$, $R_3$, and $R_4$ independently comprises hydrogen or alkyl.

11. The method of claim 10, wherein the alkyl comprises 1 to 20 carbon atoms.

12. The method of claim 1, wherein the staining reagent comprises a fluorescent dye.

13. The method of claim 12, wherein the staining reagent comprises an intercalating fluorescent dye mixture comprising at least two fluorescent dyes.

14. The method of claim 1, wherein the nucleic acids comprise single stranded nucleic acids.

15. The method of claim 14, wherein the single stranded nucleic acids comprise DNA polynucleotides, DNA oligonucleotides and RNA polynucleotides having lengths ranging from 5 to 200 nucleotides.

16. The method of claim 14, wherein the single stranded nucleic acids comprise DNA polynucleotides, DNA oligonucleotides and RNA polynucleotides having lengths ranging from 5 to 150 nucleotides.

17. The method of claim 14, wherein the single stranded nucleic acids comprise DNA polynucleotides, DNA oligonucleotides and RNA polynucleotides having lengths ranging from 5 to 100 nucleotides.

18. The method of claim 14, wherein the single stranded nucleic acids comprise DNA polynucleotides, DNA oligonucleotides and RNA polynucleotides having lengths ranging from 5 to 50 nucleotides.

19. A method of performing electrophoresis comprising:
   introducing a sample comprising nucleic acids into an electrophoresis device comprising an electrophoresis separation medium having at least one staining reagent for staining nucleic acids and at least one urea derivative, having a general formula $R_1R_2N\text{—}CO\text{—}NR_3R_4$, wherein each of $R_1$, $R_2$, $R_3$, and $R_4$ independently comprises hydrogen or alkyl, for interacting with the staining reagent, wherein the separation medium comprises a gel adapted to suspend the staining reagent and the urea derivative;
   wherein the electrophoresis device comprises electrodes for applying an electrical field across the separation medium; and
   operating the electrodes, thereby providing an electric field across the medium which is sufficient to separate the nucleic acids in the sample.

20. The method of claim 19, wherein the urea derivative is N-methylurea, N,N'-dimethylurea, N-ethylurea, or a mixture thereof.

21. The method of claim 19, wherein the staining reagent is an intercalating dye.

22. The method of claim 19, wherein the staining reagent comprises a fluorescent dye.

23. The method of claim 19, wherein the staining reagent comprises an intercalating fluorescent dye mixture comprising at least two fluorescent dyes.

24. The method of claim 19, wherein the gel comprises Agarose.

25. The method of claim 19, wherein the gel comprises polyacrylamide, polydimethylacrylamide, polyvinylpyrrolidine, or polyethyleneoxide.

26. The method of claim 19, wherein the nucleic acids comprise single stranded nucleic acids.

27. The method of claim 26, wherein the single stranded nucleic acids comprise DNA polynucleotides, DNA oligonucleotides, and/or RNA polynucleotides.

* * * * *